(12) United States Patent
Wruck

(10) Patent No.: US 8,316,846 B2
(45) Date of Patent: Nov. 27, 2012

(54) DEVICE FOR ADSORBING AND DESORBING ANESTHETIC

(75) Inventor: Norbert Wruck, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1146 days.

(21) Appl. No.: 12/188,359

(22) Filed: Aug. 8, 2008

(65) Prior Publication Data

US 2009/0095291 A1    Apr. 16, 2009

(30) Foreign Application Priority Data

Oct. 11, 2007  (DE) .......................... 10 2007 048 891

(51) Int. Cl.
  *A61M 15/00* (2006.01)
  *A61M 16/10* (2006.01)
  *A62B 7/10* (2006.01)
  *A62B 19/00* (2006.01)
  *A62B 23/02* (2006.01)
(52) U.S. Cl. ......... 128/203.12; 128/205.12; 128/205.27; 128/910
(58) Field of Classification Search ............. 128/203.12, 128/205.12, 205.27, 910
See application file for complete search history.

(56) References Cited

U.S. PATENT DOCUMENTS

| | | | | |
|---|---|---|---|---|
| 4,989,597 A | * | 2/1991 | Werner | 128/203.12 |
| 5,471,979 A | * | 12/1995 | Psaros et al. | 128/205.28 |
| 5,520,169 A | * | 5/1996 | Georgieff et al. | 128/204.16 |
| 5,957,130 A | * | 9/1999 | Krahbichler et al. | 128/205.14 |
| 6,152,133 A | * | 11/2000 | Psaros et al. | 128/205.12 |
| 6,206,002 B1 | | 3/2001 | Lambert | |
| 6,745,771 B2 | * | 6/2004 | Castor et al. | 128/205.27 |
| 6,783,573 B2 | * | 8/2004 | Richardson | 96/6 |
| 7,077,136 B2 | * | 7/2006 | Ahlmen et al. | 128/205.27 |

FOREIGN PATENT DOCUMENTS

| EP | 0 972 534 A2 | 1/2000 |
|---|---|---|
| EP | 1 440 704 B1 | 7/2004 |

\* cited by examiner

*Primary Examiner* — Loan Thanh
(74) *Attorney, Agent, or Firm* — McGlew and Tuttle, P.C.

(57) ABSTRACT

A device for adsorbing and desorbing anesthetic shall be improved in respect of the anesthetic supply. A sampling device (16) for removing a gas volume of the breathing gas and an anesthetic dispenser (18) are connected to the breathing gas line (8) between the adsorption filter (9) and the patient (10) in such a way that the gas volume removed and the gas volume supplied are compensated.

14 Claims, 4 Drawing Sheets

DEVICE FOR ADSORBING AND DESORBING ANESTHETIC

CROSS REFERENCE TO RELATED APPLICATIONS

This application claims the benefit of priority under 35 U.S.C. §119 of German Patent Application DE 10 2007 048 891.4 filed Oct. 11, 2007, the entire contents of which are incorporated herein by reference.

FIELD OF THE INVENTION

The present invention pertains to a device for supplying a patient with breathing gas with a filter device for the adsorption and desorption of anesthetic and with a breathing gas line between the filter device and the patient.

BACKGROUND OF THE INVENTION

Devices for recycling expired anesthetic are known from the state of the art and are based on the principle that expired gas is sent over a filter, which adsorbs expired anesthetic and fresh breathing gas is sent subsequently over the filter during a desorption phase in order to enrich it with previously stored anesthetic.

A device of this class is known from U.S. Pat. No. 6,206,002 B1. A patient is connected via a breathing gas line to a filter device for adsorbing and desorbing anesthetic. Fresh breathing gas arrives now at the patient from a breathing gas source via the filter device and a breathing gas line. The breathing gas is mixed with anesthetic by means of an anesthetic source in the vicinity of the patient. The anesthetic breathed out by the patient is adsorbed in the filter device during the phase of expiration and mixed again with the gas to be breathed in during the next inspiration stroke. The anesthetic consumed by the patient during stationary operation and the anesthetic not adsorbed by the filter device during the phase of expiration are replaced with the anesthetic source. Anesthetic is mixed with the breathing gas in the liquid form during the phase of expiration, and only special anesthetic dispensing devices can therefore be used. The dispensing of liquid anesthetic in the vicinity of the patient requires a great effort in terms of monitoring of the release of concentration.

EP 1 440 704 B1 discloses a device for the recycling of anesthetic, in which an adsorption filter is moved between two gas channels in order to alternatingly expose a same section of the filter to the interior of each channel. Since separate channels are present in this device for the gas to be breathed in and the expired gas, the dead space volume decreases to the volume of the filter sections that are staggered between the gas channels. However, more specific data on how the anesthetic is fed to the patient cannot be found in the document. It is also disadvantageous in the prior-art device that a rinsing gas is needed during a rapid phase of termination in order to rinse through the adsorption beds and to remove the anesthetic.

SUMMARY OF THE INVENTION

The basic object of the present invention is to improve a device of the type mentioned such that the supply of anesthetic is made possible with a plurality of anesthetic dispensers.

According to the invention, a device is provided for supplying a patient with breathing gas, the device comprises a filter device for the adsorption and desorption of anesthetic. A breathing gas line is provided between the filter device and the patient. A sampling device is connected to the breathing gas line for sampling breathing gas. An anesthetic dispensing device is connected to the breathing gas line to provide a compensation between a gas volume removed and a gas volume fed in the device.

The sampling device may comprise an anesthetic measuring device. The gas sampling device may also comprise a breathing gas source for the anesthetic dispensing device.

A gas analysis port may be provided for gas sampling, for connecting the sampling device. The gas analysis port is arranged between a connecting branch to an anesthetic supply of the anesthetic dispensing device and the patient. The gas analysis port may also be provided between a connecting branch to an anesthetic supply of the anesthetic dispensing device and the filter device.

The breathing gas line may comprise separate line sections for the gas to be inspired and gas to be expired.

Provisions are made according to the present invention for breathing gas enriched with anesthetic vapor to be introduced into the breathing gas line between the filter device and the patient and for a gas volume to be drawn off with a sampling device for breathing gas in such a way that it corresponds to the breathing gas volume fed with the anesthetic dispenser. Thus, the inspired volume is not changed in terms of the volume balance, because there is a corresponding gas volume, which is again drawn off with the sampling device in the form of a sampling pump, against the breathing gas volume enriched with anesthetic, which is additionally fed into the breathing gas line. A plurality of commercially available dispensing systems can be used due to the use of anesthetic dispensers, which need breathing gas for dispensing anesthetic. These include all the anesthetic evaporators, which operate according to the bypass principle and in which a part of the breathing gas is branched off from a bypass line and sent through an evaporating chamber for enrichment with anesthetic vapor. Furthermore, dispensing systems for highly volatile anesthetics, such as desflurane, which are based on a differential pressure regulation of two gas flows, are suitable. Due to the feed of breathing gas enriched with anesthetic and the drawing off of a corresponding compensation volume, the volume of the anesthetic being fed can be better adapted to the patient's needs.

It is especially advantageous to combine the sampling device with an anesthetic measuring device, which is needed anyway, and to feed the breathing gas drawn off directly into the anesthetic dispenser.

The gas analysis port for the sampling device is advantageously arranged between the connecting branch for the anesthetic feed and the patient. However, it is also possible, as an alternative, to provide the gas analysis port for the sampling pump directly at the filter device.

Separate line sections for the breathing gas and the expired gas are advantageously provided in the area of the breathing gas line. The gas flow is controlled by means of switchover valves such that the overwhelming majority of the gas to be breathed in flows through an inspiration channel section and the expired gas enters an expiration channel section. The anesthetic dispensing is advantageously carried out in the expiration channel section. Both the anesthetic expired by the patient and the anesthetic newly fed in are stored in this manner in the adsorber bed of the filter device during the expiration phase. The anesthetic is again released into the gas to be inspired during the next inspiration stroke. A uniform supply of anesthetic into the breathing gas is thus achieved.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
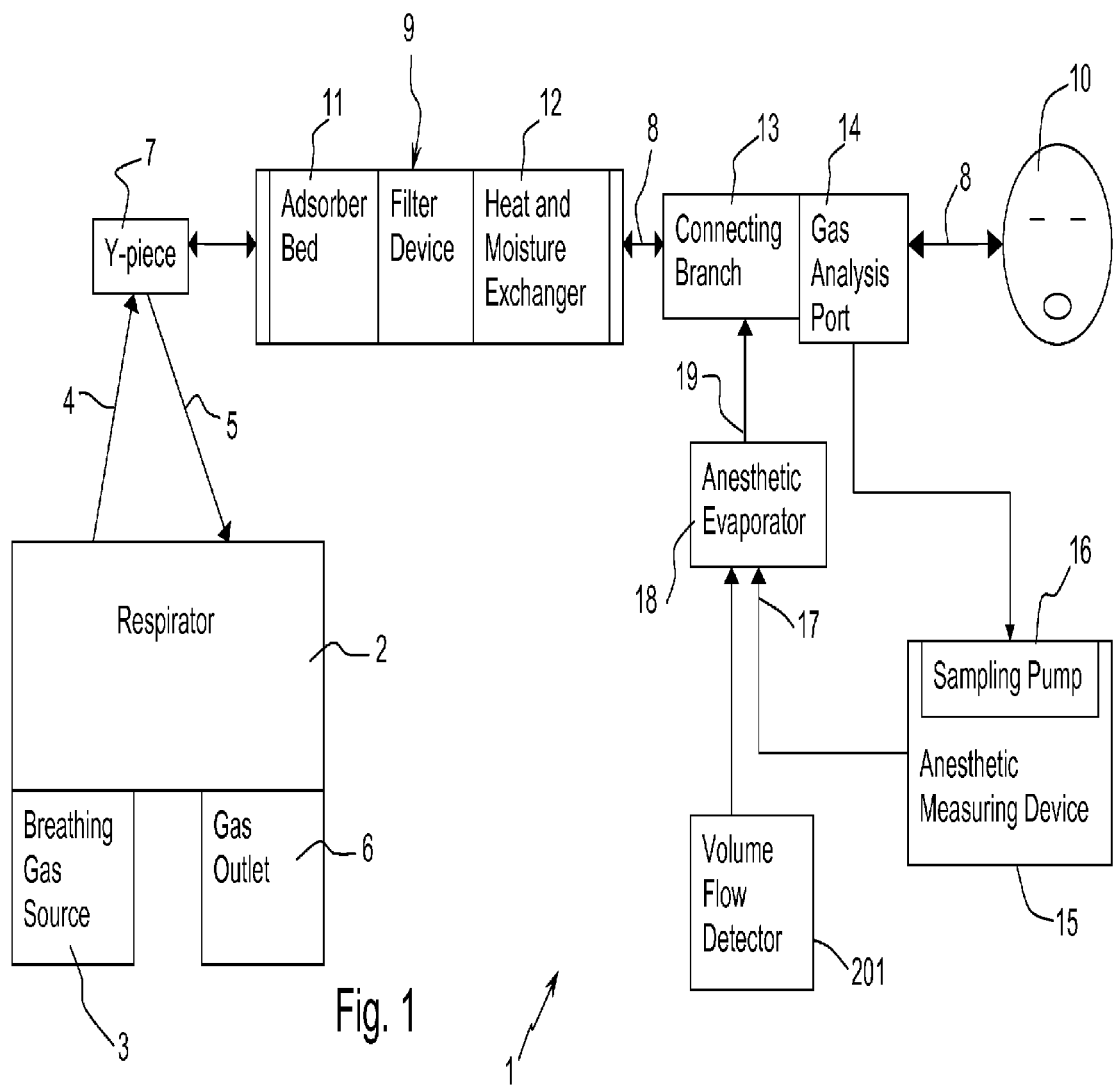
FIG. 1 is a schematic view showing a first device according to the present invention with an anesthetic dispenser.

Referring to the drawings in particular, FIG. 1 schematically illustrates the design of a first device 1 according to the present invention with a respirator (also known as a ventilator) 2. The respirator 2 is connected to a breathing gas source 3 and dispenses breathing gas in an inspiration line. Expired breathing gas enters, via an expiration line 5, a gas outlet 6 with a waste gas disposal, not shown more specifically.

The inspiration line 4 and the expiration line 5 are connected to one another via a Y-piece 7, and a breathing gas line 8 between a filter device 9, arranged downstream of the Y-piece 7 and a patient 10, supplies the patient 10 with breathing gas. The filter device 9 contains an adsorber bed 11 for adsorption and desorption of anesthetic and a heat and moisture exchanger 12, which adsorbs moisture present in the breathing gas during the expiration phase and releases same into the breathing gas again during the next inspiration stroke. Expired anesthetic is retained in the adsorber bed 11, which consists of activated carbon fibers, and is again fed into the gas to be inspired during a desorption phase at the time of the next inspiration stroke.

A connecting branch 13 for feeding the anesthetic and a gas analysis port 14 are arranged in the breathing gas line 8. The gas analysis port 14 is located in the vicinity of the patient between the patient 10 and the connecting branch 13. An anesthetic measuring device 15, connected to the gas analysis port 14 contains a sampling pump 16, which draws in breathing gas continuously from the breathing gas line 8 and passes same on to the gas inlet 17 of an anesthetic evaporator 18. The anesthetic evaporator 18, which operates according to the bypass principle, adds anesthetic vapor to the breathing gas drawn off and is connected by its gas outlet 19 to the connecting branch 13 of the breathing gas line 8. A volume flow detector 201 monitors the gas volume drawn off by the sampling pump 16. The anesthetic measuring device 15 contains a gas analyzer, with which the constituents of the breathing gas, such as the oxygen concentration, the carbon dioxide concentration and the anesthetic concentration, are determined.

An anesthetic evaporator operated according to the bypass principle is shown as an example in DE 196 13 754 C1 (corresponding to U.S. Pat. No. 5,671,729). As an alternative to an anesthetic evaporator, it is also possible to use an anesthetic dispenser for anesthetics with a low boiling point, such as desflurane, as it is described as an example in DE 10 2004 054 416 B3 (U.S. 2006065269). Reference is expressly made to the entire disclosure contents of DE 196 13 754 C1 and DE 10 2004 054 416 B3. U.S. Pat. No. 5,671,729 and U.S. 2006065269 are hereby incorporated by reference in their entirety.

Figure 2:
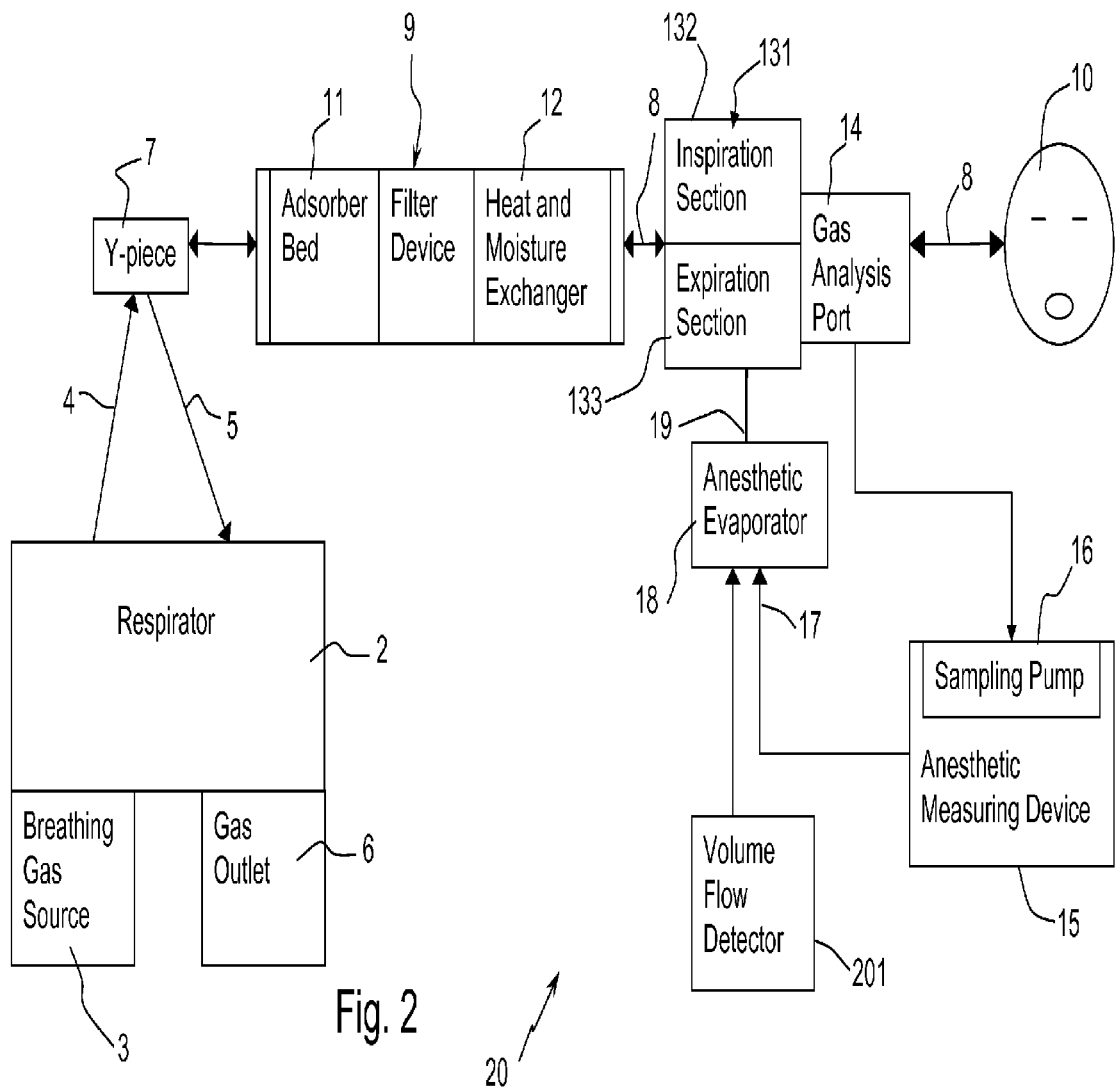
FIG. 2 is a schematic view showing an alternative device to FIG. 1, in which separate gas channels are provided for gas to be inspired and expired gas.

FIG. 2 illustrates a second device 20, which is provided with an alternative connecting branch 131 for anesthetic compared to the first device. Identical components are designated by the same reference numbers as in FIG. 1. The alternative connecting branch 131 has an inspiration channel section 132, through which predominantly gas to be inspired flows, and an expiration channel section 133 for the expired gas. The connecting branch 131 contains switchover valves, not shown more specifically, which send the gas to be inspired and the expired gas through the corresponding channel sections 132, 133. The anesthetic is dispensed directly into the expiration channel section 133, so that it is stored at first in the adsorber bed 11 at the end of the expiration stroke. The anesthetic is again released into the gas to be inspired during the desorption phase during the next inspiration stroke. Concentration peaks in the gas to be inspired are avoided due to the intermediate storage of the anesthetic dispensed in the adsorber bed 11.

Figure 3:
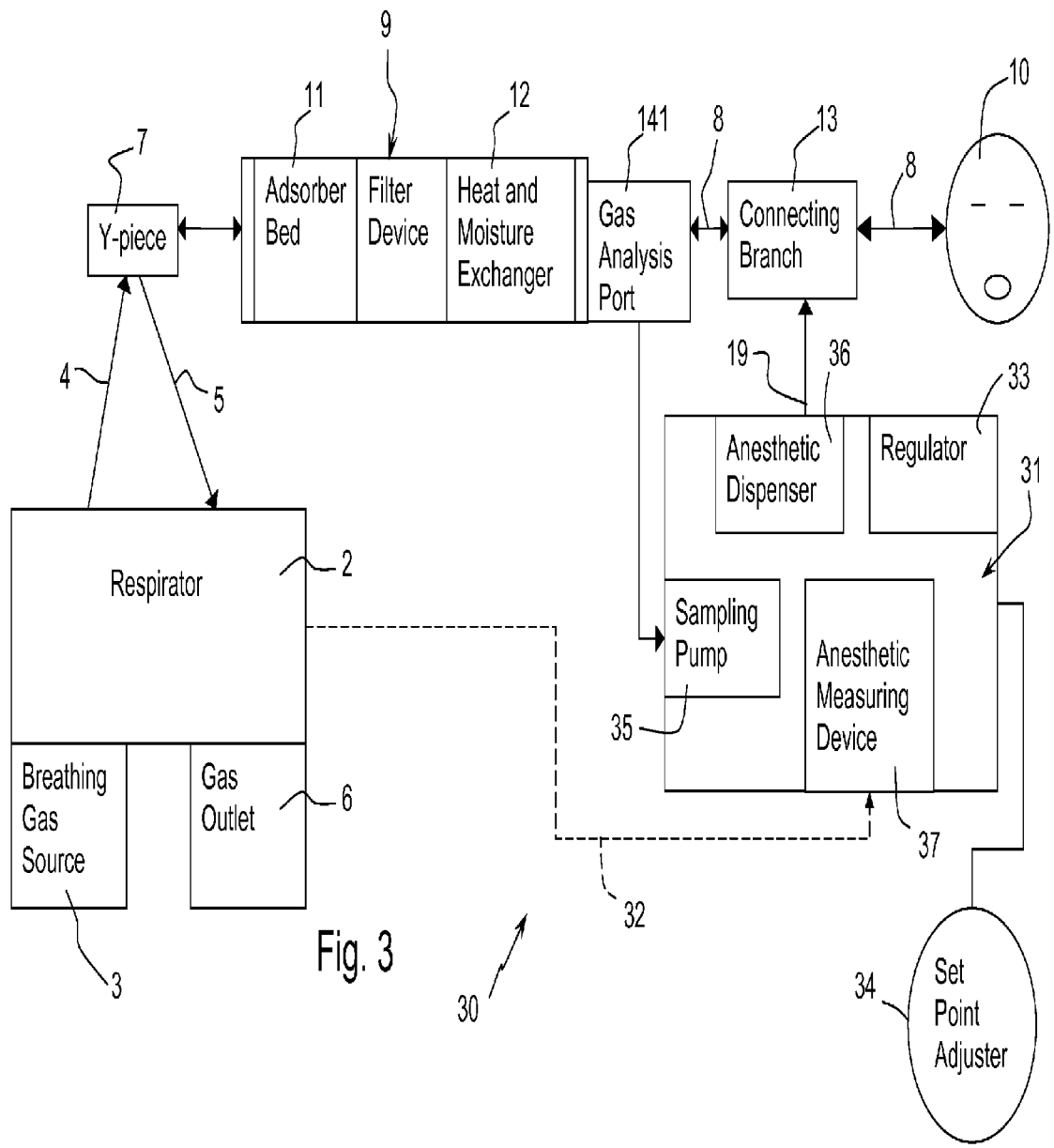
FIG. 3 is a schematic view showing a device with regulation of the anesthetic dispensing.

FIG. 3 shows a third device 30, in which a gas analysis port 141 is arranged, compared to the first device 1 according to FIG. 1, directly behind the filter device 9. The gas sampling, gas analysis and anesthetic supply take place via a combination device 31, which contains, in a modular design, a sampling pump 35, an anesthetic dispenser 36 and an anesthetic measuring device 37. The combination device 31 is connected to the respirator 2 via a signal line 32. Data of the respirator 2 are transmitted via this signal line 32 to the combination device 31, which is suitable for making it easier for the user to set the anesthetic concentration. These data are, for example, the respiratory minute volume, the peak flow, the patient's body weight and the patient's age. The combination device 31 contains a regulator 33, which is designed, in conjunction with a set point adjuster 34 for the anesthetic concentration, to set a predetermined anesthetic concentration in the breathing gas.

Figure 4:
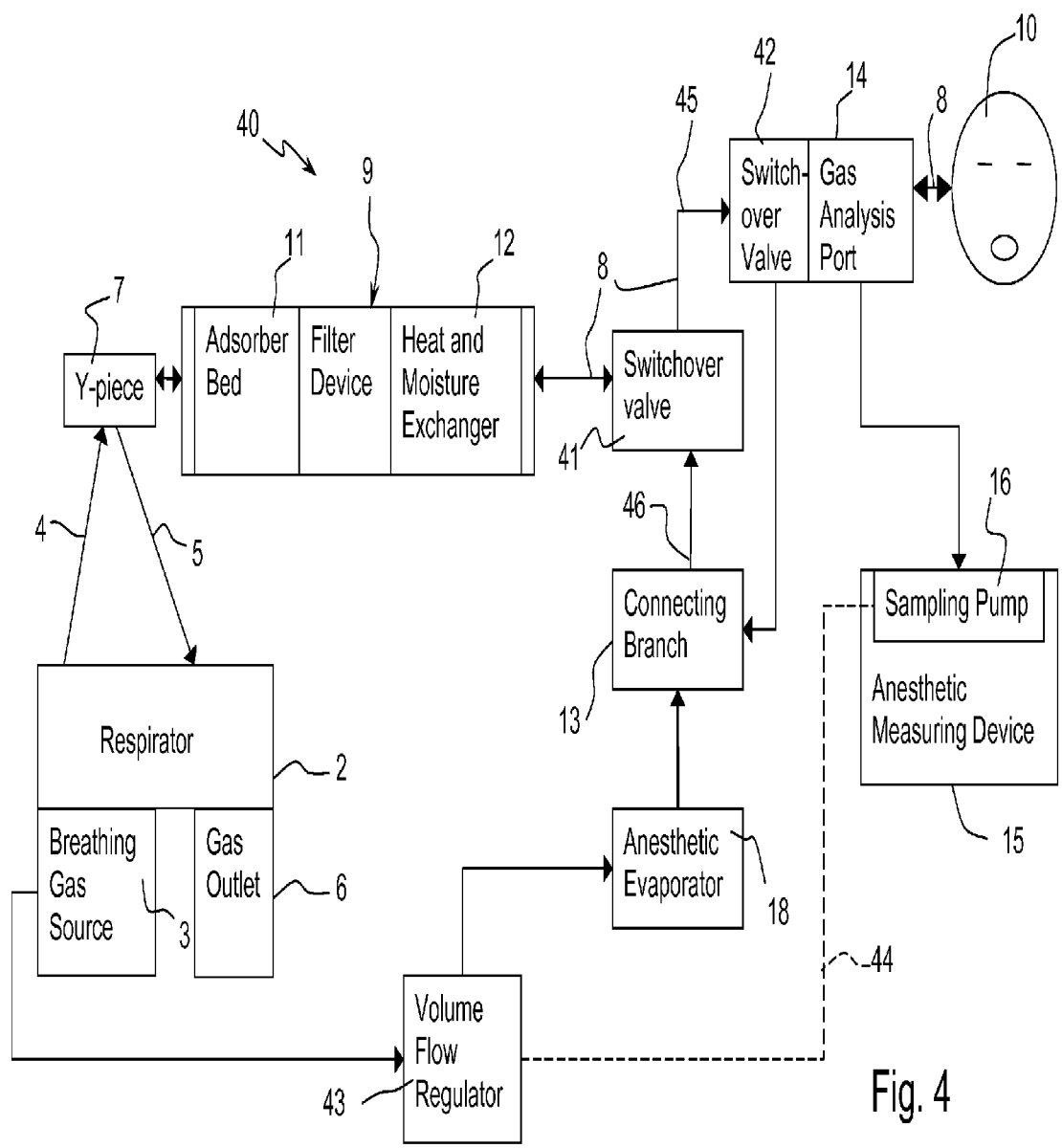
FIG. 4 is a schematic view showing a device with an anesthetic dispenser, which is supplied from an external gas source.

In a fourth device 40 corresponding to FIG. 4, the gas to be inspired is sent by means of switchover valves 41, 42 via a first gas path 45, and the expired gas is sent back to the filter device 9 via a second gas path 46. The connecting branch 13 for the anesthetic supply is arranged in the second gas path 46, so that the anesthetic enters the expired gas only. The gas for the anesthetic evaporator 18 is removed from the breathing gas source 3 via a volume flow regulator 43. Compensation between the gas volume drawn off and the gas volume fed in is carried out via a data line 44 between the volume flow regulator 43 and the sampling pump 16, so that the volume balance is compensated.

While specific embodiments of the invention have been shown and described in detail to illustrate the application of the principles of the invention, it will be understood that the invention may be embodied otherwise without departing from such principles.

APPENDIX

List of Reference Numbers

1 First device
2 Respirator
3 Breathing gas source

4 Inspiration line
5 Expiration line
6 Gas outlet
7 Y-piece
8 Breathing gas line
9 Filter device
10 Patient
11 Adsorber bed
12 Heat and moisture exchanger
13, 131 Connecting branch
132 Inspiration channel section
133 Expiration channel section
14, 141 Gas analysis port
15, 37 Anesthetic measuring device
16, 35 Sampling pump
17 Gas inlet
18 Anesthetic evaporator
19 Gas outlet
201 Volume flow detector
20 Second device
30 Third device
31 Combination device
32 Signal line
33 Regulator
34 Set point adjuster
36 Anesthetic dispenser
40 Fourth device
41, 42 Switchover valve
43 Volume flow regulator
44 Data line

What is claimed is:

1. A device for supplying a patient with breathing gas, the device comprising:
    a filter device for the adsorption and desorption of anesthetic;
    a breathing gas line between said filter device and the patient;
    a sampling device connected to said breathing gas line for sampling breathing gas to provide a removed gas volume;
    an anesthetic dispensing device connected to said breathing gas line to provide a compensation between the removed gas volume and a gas volume fed in the device; and
    a sampling pump connected to said sampling device and feeding said removed gas volume to said anesthetic dispensing device and feeding the removed gas volume with anesthetic to said breathing gas line as a gas volume fed into said breathing gas line for generating a compensation between said removed gas volume and the gas volume fed into said breathing gas line.

2. A device in accordance with claim 1, wherein said sampling device comprises an anesthetic measuring device.

3. A device in accordance with claim 1, further comprising a gas analysis port for gas sampling for said sampling device, said gas analysis port being arranged between a connecting branch to an anesthetic supply of said anesthetic dispensing device and the patient.

4. A device in accordance with claim 1, further comprising a gas analysis port for gas sampling for said sampling device, said gas analysis port being provided between a connecting branch to an anesthetic supply of said anesthetic dispensing device and said filter device.

5. A device in accordance with claim 1, wherein said sampling device comprises a breathing gas source for said anesthetic dispensing device.

6. A device in accordance with claim 1, wherein said breathing gas line comprises separate line sections for the gas to be inspired and gas to be expired.

7. A device according to claim 1, wherein:
    said breathing gas line between said filter device and the patient includes a first channel section through which predominantly gas to be inspired flows and a second channel section for expired gas; and
    said anesthetic dispensing device is connected to said second channel section to feed said gas volume fed into the breathing gas line to said second channel section.

8. A breathing system for supplying a patient with breathing gas, the system comprising:
    a respirator connected to a breathing gas source;
    a filter device for the adsorption and desorption of anesthetic, said filter device being connected to said respirator;
    a breathing gas line between said filter device and the patient;
    a sampling device connected to said breathing gas line for sampling breathing gas to remove a gas volume;
    an anesthetic dispensing device connected to said breathing gas line; and
    a sampling pump connected to said sampling device and feeding said removed gas volume to said anesthetic dispensing device and feeding the removed gas volume, enriched with anesthetic, into said breathing gas line for generating a compensation between said removed gas volume and a gas volume fed into said breathing gas line.

9. A system in accordance with claim 8, wherein said sampling device comprises an anesthetic measuring device.

10. A system in accordance with claim 8, further comprising a gas analysis port for connection of said sampling device for gas sampling, said gas analysis port being arranged between a connecting branch to an anesthetic supply of said anesthetic dispensing device and the patient.

11. A system in accordance with claim 8, further comprising a gas analysis port for connection of said sampling device for gas sampling, said gas analysis port being provided between a connecting branch to an anesthetic supply of said anesthetic dispensing device and said filter device.

12. A system in accordance with claim 8, wherein said sampling device comprises a breathing gas source for said anesthetic dispensing device.

13. A system in accordance with claim 8, wherein said breathing gas line comprises separate line sections for the gas to be inspired and gas to be expired.

14. A system according to claim 13, wherein:
    said anesthetic dispensing device is connected to said separate line section for the gas to be expired and said gas volume fed into the breathing gas line is fed to said separate line section for the gas to be expired.

* * * * *